United States Patent [19]

Hodgson

[11] Patent Number: 4,600,381

[45] Date of Patent: Jul. 15, 1986

[54] ORTHODONTIC BRACKET REMOVER

[76] Inventor: Edward W. Hodgson, 7322 Ravinia, St. Louis, Mo. 63121

[21] Appl. No.: 727,146

[22] Filed: Apr. 25, 1985

[51] Int. Cl.[4] .............................................. A61C 7/00
[52] U.S. Cl. ........................................................ 433/4
[58] Field of Search ............................ 433/4, 159, 160

[56] References Cited

U.S. PATENT DOCUMENTS 442,107  12/1890  Davison ............................. 433/159

Primary Examiner—Robert Peshock
Attorney, Agent, or Firm—Gravely, Lieder & Woodruff

[57] ABSTRACT

A bracket remover tool for orthodontic work having a lower beak for positioning alongside the base of a bracket and bearing against the surface of the tooth to which the bracket is applied and an upper beak for engaging the bracket whereby separation of the beaks will apply force to the bracket for its removal without applying twisting forces to the tooth. The lower beak may be bifurcated and the upper beak is positioned inside the bifurcations and adjacent to one of the bifurcations. Both beaks are laterally offset with respect to the centerlines of the tool.

7 Claims, 13 Drawing Figures

ORTHODONTIC BRACKET REMOVER

BACKGROUND OF THE INVENTION

This invention relates to the orthodontic field and particularly relates to the removal of brackets secured to the teeth by a process known as "bonding".

The practice of orthodontia includes the securing of brackets to teeth by bonding, usually with cement. Orthodontists use these brackets to carry straightening wires. The securing of these brackets, which may be of metal or plastic and which are attached by cement, is an improvement in the resulting attachment of the brackets to the face of the tooth. Although the adhesion of the cement to the tooth surface is quite good, the removal of these brackets by conventional tools is extremely difficult due to the adhesion of the cement to the tooth.

There are several tools described in the patent literature which address the problem of removing these brackets from teeth. Among these are Northcutt U.S. Pat. No. 3,755,902 which utilizes a pliers-type tool in which a chisel edge cleaves the onlay from the tooth and the other jaw of the pliers bears against the biting edge of the tooth. Cusato U.S. Pat. No. 3,986,265 also utilizes a pliers-type tool with chisel edges on both jaws to pry the brackets from the tooth. Cusato also utilizes a plastic cover which fits over one jaw so that this jaw can be engaged with the biting edge of the tooth and the chisel edge on the other jaw used to scrape cement from the tooth. Hoffman U.S. Pat. No. 3,911,583 shows a pliers-type instrument for removing bands and cement from a tooth. Hoffman utilizes one jaw or beak as a pivot or fulcrum against the occlusal surface of the tooth and the other jaw or beak has a scaping edge to remove the bracket or cement from the tooth. Kurz U.S. Pat. No. 4,248,587 describes a variety of orthodontic tools for removing brackets from teeth with one of the jaws having means for engaging the top of the tooth while the device is being used. Kricker U.S. Pat. No. 326,909 and Manuel U.S. Pat. No. 4,189,839 show tools with bifurcated jaws, while Shiner U.S. Pat. No. 2,985,962 and Angle U.S. Pat. No. 1,299,103 show tools for removing bands from around the tooth. There also is commercially available a tool in which a wire is hooked to a wing of a bracket and is pulled against a pair of legs which bear against the tooth. This device is effective only in certain areas of the mouth.

Many of the known tools have the impediment that they tend to impart a twisting or bending motion to the tooth, to the discomfort of the patient and sometimes result in damage to the tooth.

Accordingly, it is a principal object of this invention to provide an orthodontic tool for removing brackets cemented to the surface of the tooth.

Another object of this invention is to provide a bracket remover having a pliers-like structure with bifurcated lower jaw for engaging the tooth surface to which the bracket is cemented and a second jaw shaped to engage the bracket, whereby when the jaws are separated, sufficient force is generated to break the cement bond and free the bracket from the tooth.

Still another object is to provide a tool which can be used to remove both wing and Begg type brackets utilizing a lower beak which straddles the bracket and bears against the tooth surface to which the bracket is attached and an upper beak which engages the bracket and acts against the lower jaw to urge the bracket away from the tooth.

Still a further object of this invention is to provide an instrument having a bifurcated lower jaw for straddling a bracket and for engaging the tooth to which the bracket is cemented and an offset upper jaw for engaging a wing on one side of the bracket and for urging the bracket away from the tooth when the jaws are separated.

Still another object is to provide an instrument having offset upper and lower beaks for operating in confined small areas whereby one beak engages the surface of a tooth to which a bracket is fastened and the other beak engages a wing on the bracket to disengage the bracket from the tooth when the beaks are separated.

These and other objects and advantages will become apparent hereinafter.

SUMMARY OF THE INVENTION

The invention is an orthodontic tool for removing a bracket cemented to the surface of a tooth, which tool has a pliers-like configuration with one jaw engaging the tooth surface to which the bracket is cemented and the other jaw defining a beak which engages the bracket so that urging the jaws apart will strip the bracket from the tooth.

DESCRIPTION OF THE DRAWINGS

In the accompanying drawings which form part of the specification and wherein like numerals and letters refer to like parts wherever they occur.

DETAILED DESCRIPTION

Figure 1:
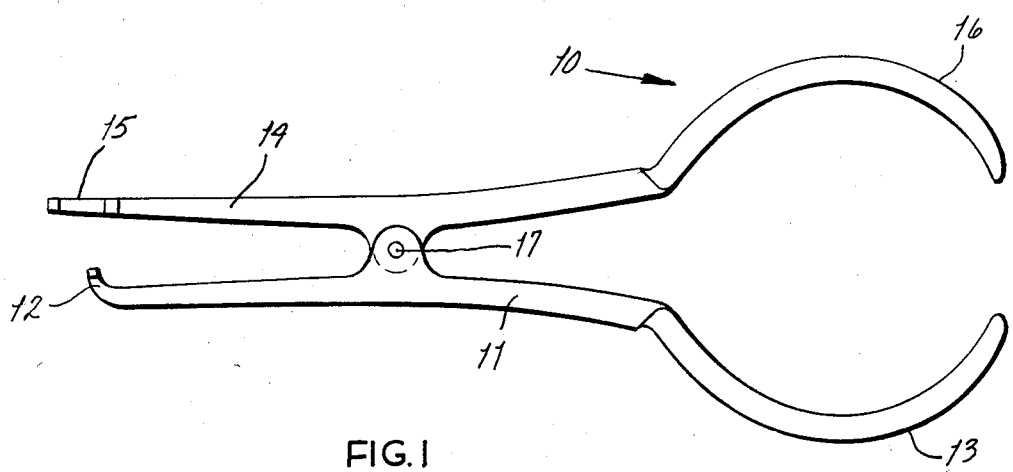
FIG. 1 is a side elevational view of the tool of this invention.

FIG. 1 shows a preferred form of the invention embodied in a pliers-like device 10 which comprises an upper jaw 11 having an offset bracket engaging end 12 and a handle 13. The lower jaw 14 has an offset bifurcated end 15 adapted to bear against the surface of a tooth and a handle 16. A pivot 17 connects the jaws 11 and 14. Urging the handles 13 and 16 together separates the jaws 12 and 15.

Figure 2:
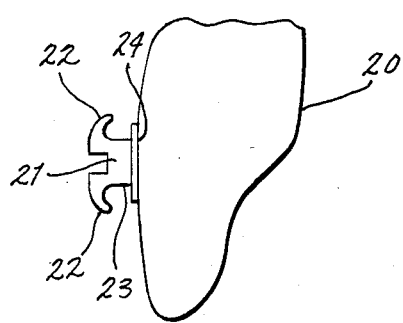
FIG. 2 is a fragmentary side elevational view of a wing bracket fastened to a tooth.
Figure 3:
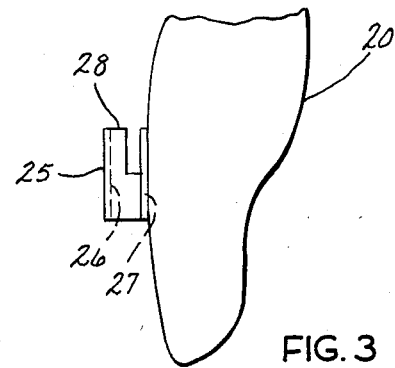
FIG. 3 is a fragmentary side elevational view of a different bracket shape fastened to a tooth.
Figure 4:
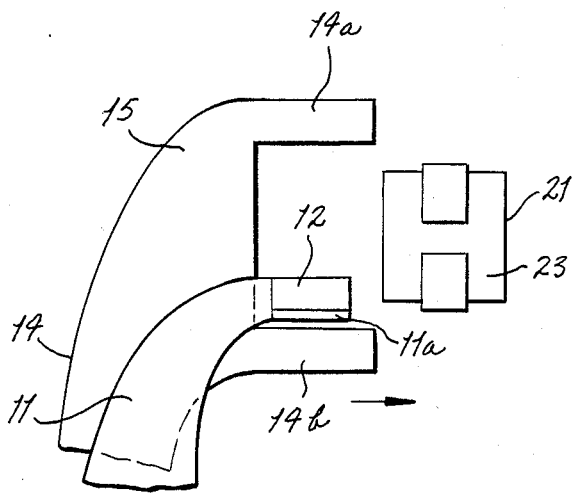
FIG. 4 is a fragmentary plan view of the tool of this invention prior to engaging an edgewise bracket.

FIGS. 2 and 3 show teeth 20 with different types of brackets mounted thereon. FIG. 2 shows a bracket 21 with wings 22 spread out from a body section 23 which is secured by a suitable cement 24 to the surface of the tooth 20.

FIG. 3 shows a barrel or "U" shaped bracket 25 having a throughbore opening 26 in the body and secured by cement 27 to the surface of the tooth 20. The bracket 25 is known as a "Begg" bracket and includes only one wing 28.

The brackets 21 and 25 are the general types of brackets in use today in orthodontics.

FIGS. 4-7 show the tool of FIG. 1 in use with a bracket like that shown in FIG. 2. The lower jaw or beak 14 is bifurcated at its leading edge and the two legs 14a and 14b fit around the bracket base 23 adjacent to the surface of the tooth 20. The uppe beak 11 has a slightly raised side edge 11a and is of lesser width than the lower beak 14 so that it will fit in the slot defined by the legs 14a and 14b. The upper beak 11 is off center in the opening between the legs 14a and 14b so that the beak 11 can engage the undersurface of the bracket wing 22 while the legs 14a and 14b straddle the bracket 21. Both of the beaks 12 and 15 are offset at about 135°-150° from the jaws 11 and 14 respectively and also angle downwardly as may be seen in FIGS. 6 and 7. These angular displacements from the centerlines of the jaws 11 and 14 allow easier access too difficult to reach teeth.

Figure 5:
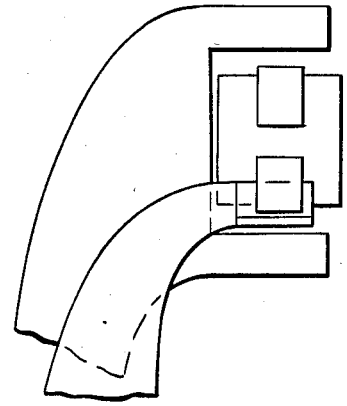
FIG. 5 is a fragmentary plan view of the tool of this invention engaged with the wing of a bracket.
Figure 6:
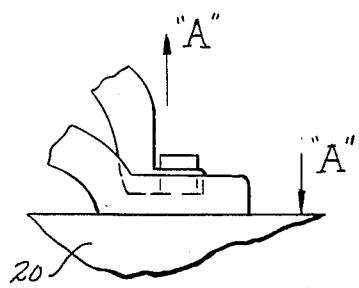
FIG. 6 is a fragmentary side elevational view of the tool and bracket engaged as in FIG. 5.
Figure 7:
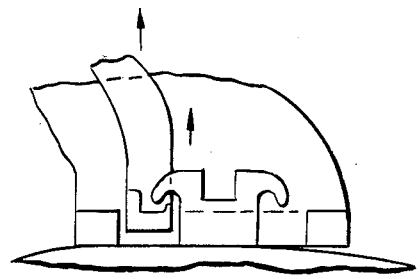
FIG. 7 is a fragmentary end view of the tool engaged with an edgewise bracket.
Figure 8:
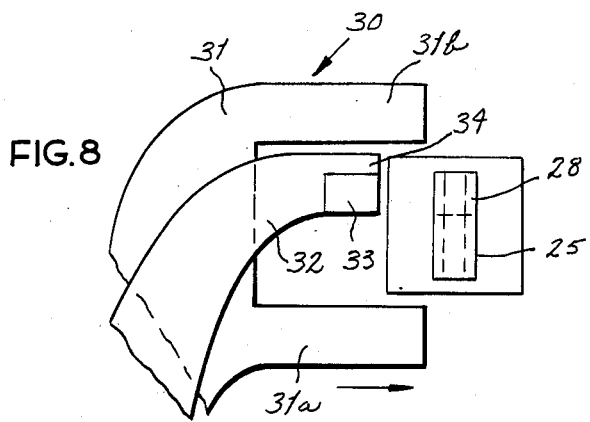
FIG. 8 is a fragmentary plan view of a modified tool of this invention before engagement with a Begg bracket.

FIG. 5 shows the tool 10 slid into position where the beak 12 engages the under surface of a bracket wing 22 so that when the jaws 11 and 14 are moved away from each other in the directions of the arrows "A" in FIG. 6, the bracket 21 is broken away from the tooth surface.

Figure 9:
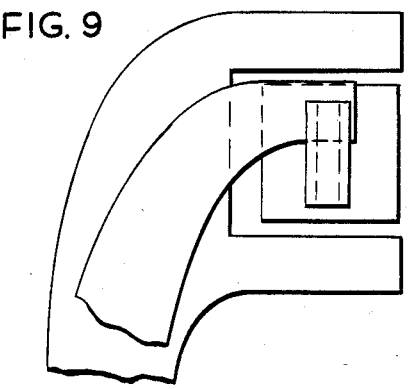
FIG. 9 is a fragmentary view of the tool of FIG. 8 engaged with a Begg bracket.

A variation of the tool is shown in FIGS. 8-11 which shows a tool 30 usable with the "Begg" bracket shown in FIG. 3. The modified tool 30 has an offset bifurcated lower beak 31 and an offset upper beak 32 which has a nose 33 thereon which is designed to be positioned beneath the wing 28 of the bracket 25 (FIG. 9). The legs 31a and 31b of the lower beak 31 straddle the bracket 25 and engage the tooth 20. When the beaks 31 and 32 are moved apart, the bracket 25 is broken away from the tooth 20.

Figure 10:
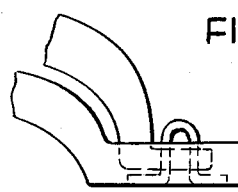
FIG. 10 is a fragmentary side elevational view of this tool of FIG. 8 engaged with a Begg bracket.
Figure 11:
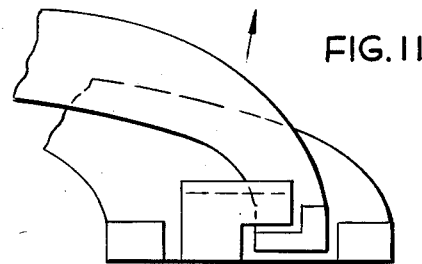
FIG. 11 is a fragmentary end view of the tool of FIG. 8 engaged with a Begg bracket.

The upper beak 33 is off center in the opening between the lower beak legs 31a and 31b so that it can be inserted beneath the bracket wing 28. As may be noted the beak 33 has a raised wall 34 along one edge which helps define a square engagement with the bracket 25. Both of the beaks 31 and 32 are offset at about 135°-150° from the centerlines of their respective jaws 14 and 11 respectively. The beaks 31 and 32 also angle downwardly as seen in FIGS. 10 and 11. These angular configurations help in locating the tool in hard to reach places in the mouth.

Figure 12:
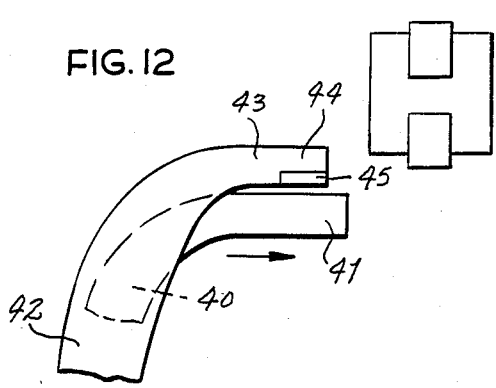
FIG. 12 is a fragmentary plan view of a modified instrument for engaging a wing bracket.
Figure 13:
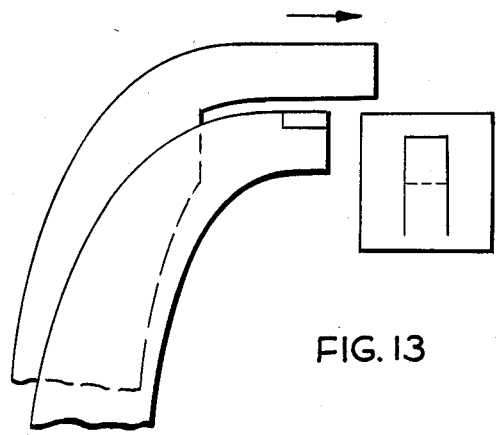
FIG. 13 is a fragmentary plan view of a modified instrument for engaging a Begg bracket.

FIGS. 12 and 13 show another variation of the invention useful in very tight situations. In this modification, the lower beak 40 is not bifurcated and has only a single bearing foot 41 which is positioned alongside the bracket and against the tooth surface. The upper jaw 42 has a beak 43 with a flat bracket wing engaging surface 44 and a locating side wall 45 adapted to be positioned against the edge of the bracket.

Any of the tools can be made in left hand or right hand embodiments. The only change is in the upper jaw and its location with respect to the lower jaw. In particular, the beaks are varied so that in the bifurcated version shown in FIGS. 4-11, the upper beak may be adjacent to the inside of either the right leg (as in FIGS. 4-7) or to the left leg (FIGS. 8-11). In either arrangement the upstanding wall on the upper beak is adjacent to the lower beak leg that is closest to the upper beak.

A similar situation exists for the tools of FIGS. 12 and 13 in which, in essence, one leg of the bifurcated lower beak has been eliminated, thus allowing use of the tool in closer quarters. In these modifications, the upraised wall of the upper beak is adjacent to the lower beak and separates the bracket engaging surface of the upper beak from the lower beak where it engages the tooth surface. The side of the lower beak leg on which the upper beak is positioned determines whether the tool is a left hand or right hand tool.

The present invention is intended to include all changes and modifications of the examples of the invention herein chosen for purposes of disclosure, which do not constitute departures from the spirit and scope of the invention.

What is claimed is:

1. In the combination of an orthodontic bracket adhesively bonded to the surface of a tooth and a tool for removing said bracket wherein said bracket has a body section which has a base surface secured to the tooth surface and at least one wing element extending outwardly from the body over the tooth surface, said wing element having an undersurface in spaced relationship to the tooth surface, the improvement comprising a tool for removing the orthodontic bracket from the surface of the tooth which comprises
   (a) first and second sections pivotally connected together to define first and second handles and first and second jaws for the tool,
   (b) a head formed on the free end of one of the jaws for engaging the outer surface of the tooth adjacent to the base of the bracket adhesively secured thereto, the head fitting alongside a side edge of the bracket base on the tooth to which the base is bonded, and
   (c) a bracket engaging beak on the free end of the second jaw for engaging the undersurface of the bracket wing, wherein separation of the jaws will urge the bracket away from the tooth surface,
   (d) the head and beak being laterally offset with respect to the centerlines of the jaws and handles.

2. The tool of claim 1 wherein the jaw head is bifurcated and fits against the surface of the tooth around the base of the bracket which is engaged by the second jaw beak, and the second jaw beak is offcenter with respect to the bifurcations and positioned within the bifurcations and adjacent to one such bifurcation.

3. The tool of claim 2 wherein the second jaw beak has a flat portion for engaging the underside of the bracket wing and an upraised wall adjacent to the said bifurcation.

4. The tool of claim 1 wherein the head and beak are offset an angle of about 135°-150°.

5. The tool of claim 1 wherein the second beak is also offset vertically from the centerline of the second jaw and handle.

6. The combination of an orthodontic bracket adhesively bonded to the surface of a tooth and a tool for removing said bracket, wherein the bracket has a body section which has a base surface secured to the tooth surface and at least one wing element extending outwardly from the body over the tooth surface, said wing element having an undersurface in spaced relationship to the tooth surface, the tool for removing the orthodontic bracket from the surface of the tooth comprising first and second sections pivotally connected together to define first and second handles and first and second jaws for the tool, a head formed on one of the jaws for engaging the outer surface of the tooth adjacent to the base of the bracket which is adhesively secured thereto, the head having a flat portion fitting on the tooth surface alongside a side edge of the bracket base which is secured to the said tooth surface, and being positioned substantially perpendicular to the centerline of the jaw and handle in a lateral direction and a bracket engaging beak on the second jaw having a flat portion for engaging the underside of the bracket wing, the beak being substantially perpendicular to the centerline of the jaw and handle in a lateral direction, wherein separation of the jaws will urge the bracket away from the tooth surface.

7. The tool of claim 6 wherein the jaw head has bifurcated flat portions so that the flat portions fit around the bracket base and engage the surface of the tooth to which the bracket is fastened and the jaw beak is offcenter with respect to the bifurcations and positioned within the bifurcations and adjacent to one such bifurcation.

* * * * *